(12) United States Patent
Crouzet et al.

(10) Patent No.: US 8,017,744 B2
(45) Date of Patent: *Sep. 13, 2011

(54) PURIFICATION OF A TRIPLE HELIX FORMATION WITH AN IMMOBILIZED OLIGONUCLEOTIDE

(75) Inventors: Joël Crouzet, Sceaux (FR); Daniel Scherman, Paris (FR); Pierre Wils, Paris (FR); Françis Blanche, Paris (FR); Béatrice Cameron, Paris (FR)

(73) Assignee: Centelion, Vitry sur Seine (FR)

( * ) Notice: Subject to any disclaimer, the term of this patent is extended or adjusted under 35 U.S.C. 154(b) by 0 days.

This patent is subject to a terminal disclaimer.

(21) Appl. No.: 12/478,418

(22) Filed: Jun. 4, 2009

(65) Prior Publication Data

US 2010/0010208 A1  Jan. 14, 2010

Related U.S. Application Data

(63) Continuation of application No. 11/253,616, filed on Oct. 20, 2005, now Pat. No. 7,622,566, which is a continuation of application No. 10/275,071, filed as application No. PCT/US01/17122 on May 25, 2001, now Pat. No. 7,038,026, which is a continuation-in-part of application No. 09/580,923, filed on May 26, 2000, now Pat. No. 6,319,672, which is a continuation-in-part of application No. 08/860,038, filed as application No. PCT/FR95/01468 on Nov. 8, 1995, now Pat. No. 6,287,762.

(30) Foreign Application Priority Data

Dec. 16, 1994 (FR) ..................................... 94 15162

(51) Int. Cl.
C07H 21/02 (2006.01)

(52) U.S. Cl. ..................................... 536/22.1; 435/6.12
(58) Field of Classification Search .................. 536/22.1; 435/6

See application file for complete search history.

(56) References Cited

U.S. PATENT DOCUMENTS

| | | | |
|---|---|---|---|
| 4,766,072 A | 8/1988 | Jendrisak et al. | |
| 5,164,491 A | 11/1992 | Froehler et al. | |
| 5,399,676 A | 3/1995 | Froehler | |
| 5,401,632 A | 3/1995 | Wang et al. | |
| 5,476,925 A | 12/1995 | Letsinger | |
| 5,478,893 A | 12/1995 | Ghosh et al. | |
| 5,482,836 A * | 1/1996 | Cantor et al. | 435/6 |
| 5,484,908 A * | 1/1996 | Froehler et al. | 536/24.31 |
| 5,591,841 A * | 1/1997 | Ji et al. | 536/25.4 |
| 5,665,541 A | 9/1997 | Miller et al. | |
| 5,800,984 A * | 9/1998 | Vary | 435/6 |
| 6,287,762 B1 | 9/2001 | Crouzet et al. | |
| 6,319,672 B1 | 11/2001 | Crouzet et al. | |
| 6,977,174 B2 | 12/2005 | Crouzet et al. | |
| 7,038,026 B2 * | 5/2006 | Crouzet et al. | 536/22.1 |
| 7,279,313 B2 | 10/2007 | Soubrier | |
| 7,364,894 B2 | 4/2008 | Soubrier | |
| 7,622,566 B2 * | 11/2009 | Crouzet et al. | 536/23.1 |

FOREIGN PATENT DOCUMENTS

| | | |
|---|---|---|
| WO | WO 89/02436 | 3/1989 |
| WO | WO 90/09393 | 8/1990 |
| WO | WO 90/10716 | 9/1990 |
| WO | WO 92/09705 | 6/1992 |
| WO | WO 92/11390 | 7/1992 |
| WO | WO 92/13963 | 8/1992 |
| WO | WO 92/18647 | 10/1992 |
| WO | WO 93/00352 | 1/1993 |
| WO | WO 93/13220 | 7/1993 |
| WO | WO 94/00600 | 1/1994 |
| WO | WO 94/17086 | 8/1994 |
| WO | WO 96/18744 | 6/1996 |
| WO | WO 2004/108167 | 12/2004 |

OTHER PUBLICATIONS

Ausubel et al., Current Protocols in Molec. Biol., Supp. 15, 1.6.1-1.6.10, 1991.
Ausubel et al., Current Protocols in Molec. Biol., Supp. 27, 1.7.1-1.7.15, 1994.
Carrière et al., "Optimization of plasmids for gene delivery," STP Pharma Sciences, 2001, vol. 11 No. 1, pp. 5-10.
Diogo, et al., "Chromatography of plasmid DNA," Journal of Chromatography A, 1069:3-22, 2005.
Duval-Valentin et al., Proc. Nat'l. Acad. Sci., USA, 89:504-508, 1992.
Faucher et al., "Quality Control of NV1FGF Plasmid DNA for PAD Gene Therapy," Standardization & QC Cell and Gene Therapy Products, for meeting held Feb. 24-25, 2003, Strasbourg, France.
He et al., Genetic Analysis Techniques & Applications, 8(3):107-110, 1991.
Ito et al., Proc. Nat'l. Acad. Sci. USA, 89:495-498, 1992.
Jarrett, Journal of Chromatography, 618(8):315-339, 1993.
Jayasena et al., Nucleic Acids Research, 20(20):5279-5288, 1992.
Ji, et al., "Rapid Purification of Double-Stranded DNA by Triple-Helix-Mediated Affinity Capture," Anal. Chem., 65:1323-1328, 1993.
Kiessling et al., Biochemistry, 31:2829-2834, 1992.
Sambrook et al., "Extraction and Purification of Plasmid DNA," Laboratory Manual, 1.21-1.52, 1987.
Talisman™ Brochure, American Heart Association, approximate date Nov. 3, 2003.
Wils, et al., "Efficient purification of plasmid DNA for gene transfer using triple-helix affinity chromatography," Gene Therapy, 4:323-330, 1997.
Presentation entitled "Gene Therapy for Ischemic Disease," by Beatrice Cameron, Sep. 23-27, 1998, Cold Spring Harbor Laboratory, New York.
Presentation entitled "FGF-1 Gene Delivery: Preliminary Clinical Results in Peripheral Vascular Disease," by Richard Pilsudski, Third Annual Angiogenesis Mini-Summit, New Orleans, La., Nov. 11, 2000.
Presentation entitled Arteriopathie des Membres Inferieurs: Quoi de neuf 2001 Therapie Genique, by Richard Pilsudski, Journees Internationales d'Angeiologie, Paris, Jan. 12-13, 2001.

(Continued)

Primary Examiner — Prabha Chunduru
(74) Attorney, Agent, or Firm — Finnegan, Henderson, Farabow, Garrett & Dunner LLP

(57) ABSTRACT

A method for double-stranded DNA purification, by which a solution containing DNA in a mixture with other components is passed over a support on which is covalently coupled an oligonucleotide capable of hybridizing with a specific sequence present on the DNA to form a triple helix.

6 Claims, No Drawings

OTHER PUBLICATIONS

Presentation entitled "Strategies for Clinical Application of Angiogenesis-Myogenesis Research," by Richard Pilsudski, 7th Local Drug Delivery Meeting and Cardiovascular Course on Radiation and Molecular Strategies, Geneva, Switzerland, Jan. 25-27, 2001.

Presentation entitled Angiogenesis: Promoting Angiogenesis: Angiogenesis Gene Therapy for Peripheral Vascular Disease, by Richard Pilsudski, Institut Pasteur Euroconferences, Paris, Mar. 8-9, 2001.

Presentation entitled "Large-Scale Purification of Plasmid DNA b Triplex Affinity Chromotography," by Francis Blanche, Recovery X, Cancun, Jun. 3-8, 2001.

Presentation entitled "Therapeutic Angiogenesis in Peripheral Vascular Disease—Final Results of the Phase I Trial on FGF-1 Gene Delivery," by Richard Pilsudski, Angiogenesis & DMR, Washington., Jun. 21-22, 2001.

Presentation entitled Purification of Plasmid DNA by Triplex Affinity Chromotography, by Francis Blanche, Downstream Processing of Nucleic Acids, Sep. 17-18, 2001.

Presentation entitled Therapeutische Angiogenese: Clinical Results of NV1FGF Gene Therapy in Chronic Limb Ischemia, by Richard Pilsudski, Angio 2001, Nov. 29-Dec. 1, 2001, Bern.

Presentation entitled "pCOR Gene Therapy Plasmid: Improvements of Existing Technology," by Fabienne Soubrier, ESGT, approximate date Oct. 13, 2002.

Presentation entitled "Final Results of a FGF-1 Gene Therapy Clinical Trial in Patients with Critical Limb Ischemia," by Marie-Helene Francois, 17th International Congress on Thrombosis, Oct. 30, 2002, Bologna, Italy.

Presentation entitled A Phase 1 Study to Evaluate the Safety and Biological Activity of Plasmid DNA Encoding FGF1 in Patients with Severe Peripheral Artery Occlusive Disease, by Michael Coleman, Angiogenesis: Gene Therapy of Cardiovascular Diseases with Angiogenic Growth Factors, SMI, Feb. 17-18, 2003, The Hatton, London.

Presentation entitled "Quality Control of NV1FGF Plasmid DNA for PAD Gene Therapy," by Didier Faucher, International Symposium organized by EDQM on Standardization and Quality Control Cell and Gene Therapy Products, EDQM meeting, Feb. 24-25, 2003, Strasbourg.

Presentation entitled "Large-Scale Production of Plasmids for Gene Therapy," by Francis Blanche, SMBC, Singapore, Apr. 20, 2004.

Presentation entitled, Treatment of Peripheral Arterial Disease with NV1FGF, Talisman™ Trials, by Michael Coleman, ,SMI, May 17-18, The Hatton, London.

Presentation entitled Talisman 105™: IM Injections of NV1FGF in CLI Patients with Planned Amputation, by Iris Baumgartner, American Heart Association, Nov. 8, 2004.

Presentation entitled Gene Therapy for the Treatment of Peripheral Arterial Disease, by Francois Meyer, ESGT, Oct. 28, 2005.

Presentation entitled "Therapeutic Angiogenesis with Intramuscular NV1FGF Improves Amputation-Free Survival in Patients with Critical Limb Ischemia," by S. Nikol et al., ACC.06 i2 Summit 2006, Mar. 11-14, Atlanta.

* cited by examiner

SEQUENCE LISTING

<160> NUMBER OF SEQ ID NOS: 36

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 1
gaggcttctt cttcttcttc ttctt                                    25

<210> SEQ ID NO 2
<211> LENGTH: 19
<212> TYPE: DNA
<213> ORGANISM: Artificial Sequence

```
<220> FEATURE:
<223> OTHER INFORMATION: Description of Artificial Sequence:
      oligonucleotide

<400> SEQUENCE: 2
cttcccgaag ggagaaagg                                              19

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 3
gaagggcttc cctctttcc                                              19

<210> SEQ ID NO 4
<211> LENGTH: 13
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 4
gaaaaaggaa gag                                                    13

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 5
aagggaggga ggagaggaa                                              19

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 6
aaggagagga gggagggaa                                              19

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 7
ttggtgtggt gggtgggtt                                              19

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence:
```

-continued oligonucleotide

<400> SEQUENCE: 8
aaaaaaggga ataaggg                                          17

<210> SEQ ID NO 9
<211> LENGTH: 58
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 9
gatccgaaga agaagaagaa gaagaagaag aagaagaaga agaagaagaa gaagaagg   58

<210> SEQ ID NO 10
<211> LENGTH: 58
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 10
aattccttct tcttcttctt cttcttcttc ttcttcttct tcttcttctt cttcttcg   58

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 11
tgaccggcag caaaatg                                          17

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence:
      oligonucleotide
<220> FEATURE:
<223> OTHER INFORMATION: all cytosines (C) in the sequence are
      methylated

<400> SEQUENCE: 12
gaggcttctt cttcttcctc ttctt                                 25

<210> SEQ ID NO 13
<211> LENGTH: 58
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 13
gatccgagag agagagagag agagagagag agagagagag agagagagag agagaggg   58

<210> SEQ ID NO 14
<211> LENGTH: 58
<212> TYPE: DNA
<213> ORGANISM: Artificial Sequence
<220> FEATURE:

<223> OTHER INFORMATION: Description of Artificial Sequence:
      oligonucleotide

<400> SEQUENCE: 14
aattccctct ctctctctct ctctctctct ctctctctct ctctctcg                58

<210> SEQ ID NO 15
<211> LENGTH: 58
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 15
gatccggagg aggaggagga ggaggaggag gaggaggagg aggaggagga ggaggagg     58

<210> SEQ ID NO 16
<211> LENGTH: 58
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 16
aattcctcct cctcctcctc ctcctcctcc tcctcctcct cctcctcctc ctcctccg    58

<210> SEQ ID NO 17
<211> LENGTH: 50
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 17
ggagaggagg aggaggagga ggaggaggag gaggaggagg aggaggagga               50

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 18
aatgcctcct cctcctcctc ctcct                                          25

<210> SEQ ID NO 19
<211> LENGTH: 26
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 19
agtgctctct ctctctctct ctctct                                         26

<210> SEQ ID NO 20
<211> LENGTH: 66
<212> TYPE: DNA
<213> ORGANISM: Artificial Sequence
<220> FEATURE:
<223> OTHER INFORMATION: Description of Artificial Sequence:
      oligonucleotide

```
<400> SEQUENCE: 20
gatctgaaga agaagaagaa gaagaagaag aagaagaaga agaagaagaa gaagaactgc        60
agatct                                                                  66

<210> SEQ ID NO 21
<211> LENGTH: 66
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 21
gatcagatct gcagttcttc ttcttcttct tcttcttctt cttcttcttc ttcttcttct        60
tcttca                                                                  66

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 22
acagtcataa gtgcggcgac g                                                 21

<210> SEQ ID NO 23
<211> LENGTH: 39
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 23
gaagaagagg aagaagaaga agaagaagaa ggaagagaa                              39

<210> SEQ ID NO 24
<211> LENGTH: 27
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 24
ccgaattctg gggaccaaag cagtttc                                           27

<210> SEQ ID NO 25
<211> LENGTH: 27
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 25
ccaagcttca ctgttcacga cgggtgt                                           27

<210> SEQ ID NO 26
<211> LENGTH: 21
<212> TYPE: DNA
<213> ORGANISM: Artificial Sequence
<220> FEATURE:
```

```
<223> OTHER INFORMATION: Description of Artificial Sequence:
      oligonucleotide

<400> SEQUENCE: 26
cttcttcttc ttcttcttct t                                              21

<210> SEQ ID NO 27
<211> LENGTH: 12
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 27
agaaaaaaag ga                                                        12

<210> SEQ ID NO 28
<211> LENGTH: 12
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 28 tcttttttc ct                                                         12

<210> SEQ ID NO 29
<211> LENGTH: 14
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 29
aagaaaaaaa agaa                                                      14

<210> SEQ ID NO 30
<211> LENGTH: 14
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 30
ttcttttttt tctt                                                      14

<210> SEQ ID NO 31
<211> LENGTH: 11
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 31 tttttttcc t                                                          11

<210> SEQ ID NO 32
<211> LENGTH: 12
<212> TYPE: DNA
<213> ORGANISM: Artificial Sequence
<220> FEATURE:
<223> OTHER INFORMATION: Description of Artificial Sequence:
      oligonucleotide
```

-continued

```
<400> SEQUENCE: 32
agaaaaaaaa ga                                                               12

<210> SEQ ID NO 33
<211> LENGTH: 51
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 33
gaagaagaag aagaagaaga agaagaagaa gaagaagaag aagaagaaga a                    51

<210> SEQ ID NO 34
<211> LENGTH: 48
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 34
ggaggaggag gaggaggagg aggaggagga ggaggaggag gaggagga                        48

<210> SEQ ID NO 35
<211> LENGTH: 50
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 35
gagagagaga gagagagaga gagagagaga gagagagaga gagagagaga                      50

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 36
gaagaagaag aagaagaaga a                                                     21
```

PURIFICATION OF A TRIPLE HELIX FORMATION WITH AN IMMOBILIZED OLIGONUCLEOTIDE

CROSS REFERENCE TO RELATED APPLICATIONS

This is a continuation of application Ser. No. 11/253,616, filed Oct. 20, 2005, which is a continuation of application Ser. No. 10/275,071, filed Apr. 7, 2003, now U.S. Pat. No. 7,038,026, which is the National Stage of International Application PCT/US01/17122, which is a continuation-in-part of U.S. application Ser. No. 09/580,923, filed May 26, 2000, now U.S. Pat. No. 6,319,672, which is a continuation-in-part application of U.S. application Ser. No. 08/860,038, filed Jun. 9, 1997, now U.S. Pat. No. 6,287,762, which is the U.S. national stage application of International Application No. PCT FR95/01468, filed Nov. 8, 1995, the contents of which are relied upon and incorporated by reference.

BACKGROUND OF THE INVENTION

The present invention relates to a new method for DNA purification. The method according to the invention enables pharmacologically usable double-stranded DNA to be purified rapidly. More especially, the purification method according to the invention involves a specific hybridization between a sequence of the DNA and an oligonucleotide.

Gene and cell therapy techniques are currently undergoing remarkable development. However, these techniques entail the possibility of producing large amounts of DNA of pharmaceutical purity. In effect, in these new therapies, the medicament often consists of DNA itself, and it is essential to be able to manufacture it in suitable amounts, to isolate it and to purify it in a manner suited to therapeutic use in man.

In recent years, the feasibility of injection of plasmid DNA for gene therapy or vaccination has been demonstrated by numerous reports demonstrating that DNA expression vectors can be taken up by various cell types and genes encoded by these plasmids can be subsequently expressed medley, 1995 Hum. Gene Ther. 6, 1129).

The genes of interest for gene therapy or vaccination applications may include, for example, tumor suppressor gene, suicide genes, or anti-sense sequences. They can also encode proteins such as alpha-fetoprotein AFP (Morinaga, 1983, Proc. Natl. Acad. Sci. USA, 80, 4604), enzymes, hormones, cytokines, growth factors such as FGF (Jouanneau et al., 1991, Proc. Natl. Acad. Sci. USA, 88, 2893) or VEGFB (Olofsson B al., 1996, Proceedings 93, 576), clotting factors such as B-deleted Factor VIII (Truett et al., 1985, DNA 4, 333), apolipoproteins, neurotransmitters, neurotrophic factors, natural or chimeric immunoglobulin. Reporter genes such as lacZ encoding the *Escherichia coli* β-galactosidase are also used.

Major challenges for using plasmid DNA as a gene delivery vector in human are i) the manufacture and ii) the purity of this drug product. Technologies for the production of plasmids vectors with high copy number in *Escherichia coli* hosts have been recently developed. The plasmids currently used are either ColE1-derived plasmids such as pBR322, pUC or pBluescript (Lahijani et al., 1996, Hum. Gene Ther., 7, 1971) or pCOR plasmids (Soubrier et al., 1999, Gene Therapy, 6, 1482).

The second concern raised by the use of plasmid DNA as a gene therapy vector is the purity of the plasmid vector itself. Current purification methods such as ultracentrifugation in CsCl gradients or chromatography can be inefficient in removing contaminants such as host genomic DNA and RNA or proteins. Particularly, host genomic DNA whose chemical structure is very close to that of plasmid DNA, is extremely difficult to remove using classical chromatography. Typical concentrations of up to 0.5 to 1% host genomic DNA are found in plasmid preparations obtained by classical chromatography. Therefore, in order to develop plasmid DNA as a safe vector for human gene therapy, there is a need for purification technologies that will lower the content of host genomic DNA down to much lower levels, typically 0.1% or even 0.01% or lower.

The present invention describes a simple and especially effective new method for DNA purification. It makes it possible, in particular, to obtain especially high purities with high yields. The method according to the invention is based essentially on a specific interaction between a sequence inserted into the DNA to be purified and an oligonucleotide composed of natural or modified bases.

It has recently been shown that some oligonucleotides are capable of interacting specifically in the wide groove of the DNA double helix to form triple helices locally, leading to an inhibition of the transcription of target genes (Hélène et Toulmé, Biochim. Biophys. Acta 1049 (1990) 99). These oligonucleotides selectively recognize the DNA double helix at oligopurine-oligopyrimidine sequences, that is to say at regions possessing an oligopurine sequence on one strand and an oligopyrimidine sequence on the complementary strand, and form a triple helix locally thereat. The bases of the third strand (the oligonucleotide) form hydrogen bonds (Hoogsteen or reverse Hoogsteen bonds) with the purines of the Watson-Crick base pairs.

A use of this type of interaction to isolate a plasmid has been described in the prior art. Thus, Ito et al. PNAS 89 (1992) 495) describe the use of biotinylated oligonucleotides capable of recognizing a particular sequence of a plasmid and of forming a triple helix therewith. The complexes thus formed are then brought into contact with streptavidin-coated magnetic beads. Interaction between the biotin and the streptavidin then enables the plasmid to be isolated by magnetic separation of the beads followed by elution. However, this method has some drawbacks. In particular, two successive specific interactions are needed, the first between the oligonucleotide and the plasmid and the second between the biotinylated complex and the streptavidin beads. Furthermore, the final solution may be contaminated with biotinylated oligonucleotide, which cannot be used in a pharmaceutical composition.

SUMMARY OF THE INVENTION

The present invention describes a new, improved method of DNA purification making use of this type of interaction. More especially, the method of the invention employs oligonucleotides coupled covalently to a support. This method is especially rapid, and it leads to especially high yields and degrees of purity. Moreover, it enables DNA to be purified from complex mixtures comprising, in particular, other nucleic acids, proteins, endotoxins (such as lipopolysaccharides), nucleases and the like. The supports used may, in addition, be readily recycled, and the DNAs obtained display improved properties of pharmaceutical safety. Lastly, this method entails only one step, contrary to the prior art.

Hence a first subject of the invention lies in a method for the purification of double-stranded DNA, according to which a solution containing the said DNA mixed with other components is passed through a support to which is coupled covalently an oligonucleotide capable of forming a triple helix by hybridization with a specific sequence present in said DNA. The specific sequence can be a sequence naturally present in the double-stranded DNA, or a synthetic sequence introduced artificially into the latter.

The oligonucleotides used in the present invention are oligonucleotides which hybridize directly with the double-stranded DNA. These oligonucleotides can contain the following bases:
- thymidine (T), which is capable of forming triplets with A.T doublets of double-stranded DNA (Rajagopal et al., Biochem 28 (1989) 7859);
- adenine (A), which is capable of forming triplets with A.T doublets of double-stranded DNA;
- guanine (G), which is capable of forming triplets with G.C doublets of double-stranded DNA;
- protonated cytosine (C+), which is capable of forming triplets with G.C doublets of double-stranded DNA (Rajagopal et al., loc. cit.);
- uracil (U), which is capable of forming triplets with A.U or A.T base pairs.
- Preferably, the oligonucleotide used comprises a cytosine-rich homopyrimidine sequence and the specific sequence present in the DNA is a homopurine-homopyrimidine sequence. The presence of cytosines makes it possible to have a triple helix which is stable at acid pH where the cytosines are protonated, and destabilized at alkaline pH where the cytosines are neutralized.

To permit the formation of a triple helix by hybridization, it is important for the oligonucleotide and the specific sequence present in the DNA to be complementary. In this connection, to obtain the best yields and the best selectivity, an oligonucleotide and a specific sequence which are fully complementary are used in the method of the invention. These can be, in particular, an oligonucleotide poly(CTT) and a specific sequence poly(GAA). As an example, there may be mentioned the oligonucleotide of sequence 5'-GAGGCT-TCTTCTTCTTCTTCTT-3' (GAGG(CTT)₇; SEQ ID NO: 1), in which the bases GAGG do not form a triple helix but enable the oligonucleotide to be spaced apart from the coupling arm; the sequence (CTT)₇ (SEQ ID No: 26) may also be mentioned. These oligonucleotides are capable of forming a triple helix with a specific sequence containing complementary units (GAA). The sequence in question can, in particular, be a region containing 7, 14 or 17 GAA units, as described in the examples.

Another sequence of specific interest is the sequence:

```
                                (SEQ. ID NO: 5)
    5'-AAGGGAGGGAGGAGAGGAA-3'.
```

This sequence forms a triple helix with the oligonucleotides

```
                                (SEQ ID No: 6)
    5'-AAGGAGAGGAGGGAGGGAA-3'
    or
                                (SEQ ID NO: 7)
    5'-TTGGTGTGGTGGGTGGGTT-3'.
```

In this case, the oligonucleotide binds in an antiparallel orientation to the polypurine strand. These triple helices are stable only in the presence of Mg$^{2+}$ (Vasquez et al., Biochemistry, 1995, 34, 7243-7251; Beal and Dervan, Science, 1991, 251, 1360-1363).

As stated above, the specific sequence can be a sequence naturally present in the double-stranded DNA, or a synthetic sequence introduced artificially in the latter. It is especially advantageous to use an oligonucleotide capable of forming a triple helix with a sequence naturally present in the double-stranded DNA, for example in the origin of replication of a plasmid or in a marker gene. In this connection, the Applicant has performed plasmid sequence analyses, and was able to show that some regions of these DNAs, in particular in the origin of replication, could possess homopurine-homopyrimidine regions. The synthesis of oligonucleotides capable of forming triple helices with these natural homopurine-homopyrimidine regions advantageously enables the method of the invention to be applied to unmodified plasmids, in particular commercial plasmids of the pUC, pBR322, pSV, and the like, type. Among the homopurine-homopyrimidine sequences naturally present in a double-stranded DNA, a sequence comprising all or part of the sequence 5'-CTTC-CCGAAGGGAGAAAGG-3' (SEQ ID NO: 2) present in the origin of replication of E. coli plasmid ColE1 may be mentioned. In this case, the oligonucleotide forming the triple helix possesses the sequence: 5'-GAAGGGCTTC-CCTCTTTCC-3' (SEQ ID NO: 3), and binds alternately to the two strands of the double helix, as described by Beal and Dervan (J. Am. Chem. Soc. 1992, 114, 4976-4982) and Jayasena and Johnston (Nucleic Acids Res. 1992, 20, 5279-5288). The sequence 5'-GAAAAAGGAAGAG-3' (SEQ ID NO: 4) of the plasmid pBR322, β-lactamase gene (Duval-Valentin et al., Proc. Natl. Acad. Sci. USA, 1992, 89, 504-508) may also be mentioned.

Two additional target sequences which can form triplex structures with particular oligonucleotides have been identified in ColE1 and in pCOR origins of replication ColE1-derived plasmids contain a 12-mer homopurine sequence (5'-AGAAAAAAAGGA-3') (SEQ ID NO: 27) mapped upstream of the RNA-II transcript involved in plasmid replication (Lacatena et al., 1981, Nature, 294, 623). This sequence forms a stable triplex structure with the 12-mer complementary 5'-TCTTTTTTTCCT-3' (SEQ ID NO: 28) oligonucleotide. The pCOR backbone contains a homopurine stretch of 14 non repetitive bases (5'-AAGAAAAAAAAGAA-3') (SEQ ID NO: 29) located in the A+T-rich segment of the γ origin replicon of pCOR (Levchenko et al., 1996, Nucleic Acids Res., 24, 1936). This sequence forms a stable triplex structure with the 14-mer complementary oligonucleotide 5'-TTCTTTTTTTTCTT-3' (SEQ ID NO: 30) The corresponding oligonucleotides 5'-TCTTTTTTTCCT-3' (SEQ ID NO: 28) and 5'-TTCTTTTTTTCTT-3' (SEQ ID NO:30) efficiently and specifically target their respective complementary sequences located within the origin of replication of either ColE1 ori or pCOR (oriγ). In fact, a single non-canonical triad (T*GC or C*AT) may result in complete destabilization of the triplex structure.

The use of an oligonucleotide capable of forming a triple helix with a sequence present in an origin of replication or a marker gene is especially advantageous, since it makes it possible, with the same oligonucleotide, to purify any DNA containing the said origin of replication or said marker gene. Hence it is not necessary to modify the plasmid or the double-stranded DNA in order to incorporate an artificial specific sequence in it.

Although fully complementary sequences are preferred, it is understood, however, that some mismatches may be tolerated between the sequence of the oligonucleotide and the sequence present in the DNA, provided they do not lead to too great a loss of affinity. The sequence 5'-AAAAAAGGGAA TAAGGG-3' (SEQ ID NO: 8) present in the E. coli β-lactamase gene may be mentioned. In this case, the thymine interrupting the polypurine sequence may be recognized by a guanine of the third strand, thereby forming a G*TA triplet which it is stable when flanked by two T*AT triplets (Kiessling et al., Biochemistry, 1992, 31, 2829-2834).

According to a particular embodiment, the oligonucleotides of the invention comprise the sequence $(CCT)_n$, the sequence $(CT)_n$ or the sequence $(CTT)_n$, in which n is an integer between 1 and 15 inclusive. It is especially advantageous to use sequences of the type $(CT)_n$ or $(CTT)_n$. The Applicant showed, in effect, that the purification yield was influenced by the amount of C in the oligonucleotide. In particular, as shown in Example 7, the purification yield increases when the oligonucleotide contains fewer cytosines. It is understood that the oligonucleotides of the invention can also combine (CCT), (CT) or (CTT) units.

The oligonucleotide used may be natural (composed of unmodified natural bases) or chemically modified. In particular, the oligonucleotide may advantageously possess certain chemical modifications enabling its resistance to or its protection against nucleases, or its affinity for the specific sequence, to be increased.

According to the present invention, oligonucleotide is also understood to mean any linked succession of nucleosides which has undergone a modification of the skeleton with the aim of making it more resistant to nucleases. Among possible modifications, oligonucleotide phosphorothioates, which are capable of forming triple helices with DNA (Xodo et al., Nucleic Acids Res., 1994, 22, 3322-3330), as well as oligonucleotides possessing formacetal or methylphosphonate skeletons (Matteucci et al., J. Am. Chem. Soc., 1991, 113 7767-7768), may be mentioned. It is also possible to use oligonucleotides synthesized with a anomers of nucleotides, which also form triple helices with DNA (Le Doan et al., Nucleic Acids Res., 1987, 15, 7749-7760). Another modification of the skeleton is the phosphoramidate link. For example, the $N^{3'}$—$P^{5'}$ internucleotide phosphoramidate link described by Gryaznov and Chen, which gives oligonucleotides forming especially stable triple helices with DNA (J. Am. Chem. Soc., 1994, 116, 3143-3144), may be mentioned. Among other modifications of the skeleton, the use of ribonucleotides, of 2'-O-methylribose, phosphodiester, etc. (Sun and Hélène, Curr. Opinion Struct. Biol., 116, 3143-3144) may also be mentioned. Lastly, the phosphorus-based skeleton may be replaced by a polyamide skeleton as in PNAs (peptide nucleic acids), which can also form triple helices (Nielsen et al., Science, 1991, 25, 1497-1500; Kim et al., J. Am. Chem. Soc., 1993, 115, 6477-6481), or by a guanidine-based skeleton, as in DNGs (deoxyribonucleic guanidine, Proc. Natl. Acad. Sci. USA, 1995, 92, 6097-6101), or by polycationic analogues of DNA, which also form triple helices.

The thymine of the third strand may also be replaced by a 5-bromouracil, which increases the affinity of the oligonucleotide for DNA (Povsic and Dervan, J. Am. Chem. Soc., 1989, 111, 3059-3061). The third strand may also contain unnatural bases, among which there may be mentioned 7-deaza-2'-deoxyxanthosine (Milligan et al., Nucleic Acids Res., 1993, 21, 327-333), 1-(2-deoxy-β-D-ribofuranosyl)-3-methyl-5-amino-1H-pyrazolo[4,3-d]pyrimidin-7-one (Koh and Dervan, J. Am. Chem. Soc., 1992, 114, 1470-1478), 8-oxoadenine, 2-aminopurine, 2'-O-methylpseudoisocytidine, or any other modification known to a person skilled in the art (for a review see Sun and Hélène, Curr. Opinion Struct. Biol., 1993, 3, 345-356).

Another type of modification of the oligonucleotide has the aim, more especially, of improving the interaction and/or affinity between the oligonucleotide and the specific sequence. In particular, a most advantageous modification according to the invention consists in methylating the cytosines of the oligonucleotide (see Example 5). The oligonucleotide thus methylated displays the noteworthy property of forming a stable triple helix with the specific sequence in pH ranges closer to neutrality ($\geq 5$). It hence makes it possible to work at higher pH values than the oligonucleotides of the prior art, that is to say at pH values where the risks of degradation of plasmid DNA are much smaller.

The length of the oligonucleotide used in the method of the invention is at least 3 bases, and preferably between 5 and 30. An oligonucleotide of length greater than 10 bases is advantageously used. The length may be adapted by a person skilled in the art for each individual case to suit the desired selectivity and stability of the interaction.

The oligonucleotides according to the invention may be synthesized by any known technique. In particular, they may be prepared by means of nucleic acid synthesizers. Any other method known to a person skilled in the art may quite obviously be used.

To permit its covalent coupling to the support, the oligonucleotide is generally functionalized. Thus, it may be modified by a thiol, amine or carboxyl terminal group at the 5' or 3' position. In particular, the addition of a thiol, amine or carboxyl group makes it possible, for example, to couple the oligonucleotide to a support bearing disulphide, maleimide, amine, carboxyl, ester, epoxide, cyanogen bromide or aldehyde functions. These couplings form by establishment of disulphide, thioether, ester, amide or amine inks between the oligonucleotide and the support. Any other method known to a person skilled in the art may be used, such as bifunctional coupling reagents, for example.

Moreover, to improve the hybridization with the coupled oligonucleotide, it can be advantageous for the oligonucleotide to contain an "arm" and a "spacer" sequence of bases. The use of an arm makes it possible, in effect, to bind the oligonucleotide at a chosen distance from the support, enabling its conditions of interaction with the DNA to be improved. The arm advantageously consists of a linear carbon chain, comprising 1 to 18 and preferably 6 or 12 ($CH_2$) groups, and an amine which permits binding to the column. The arm is linked to a phosphate of the oligonucleotide or of a "spacer" composed of bases which do not interfere with the hybridization. Thus, the "spacer" can comprise purine bases. As an example, the "spacer" can comprise the sequence GAGG. The arm is advantageously composed of a linear carbon chain comprising 6 or 12 carbon atoms.

For implementation of the present invention, different types of support may be used. These can be functionalized chromatographic supports, in bulk or prepacked in a column, functionalized plastic surfaces or functionalized latex beads, magnetic or otherwise. Chromatographic supports are preferably used. As an example, the chromatographic supports capable of being used are agarose, acrylamide or dextran as well as their derivatives (such as Sephadex, Sepharose, Superose, etc.), polymers such as poly(styrene/divinylbenzene), or grafted or ungrafted silica, for example. The chromatography columns can operate in the diffusion or perfusion mode.

To obtain better purification yields, it is especially advantageous to use, on the plasmid, a sequence containing several positions of hybridization with the oligonucleotide. The presence of several hybridization positions promotes, in effect, the interactions between the said sequence and the oligonucleotide, which leads to an improvement in the purification yields. Thus, for an oligonucleotide containing n repeats of (CCT), (CT) or (CTT) motifs, it is preferable to use a DNA sequence containing at least n complementary motifs, and preferably n+1 complementary motifs. A sequence carrying n+1 complementary motifs thus affords two positions of hybridization with the oligonucleotide. Advantageously, the DNA sequence contains up to 11 hybridization positions, that is to say n+10 complementary motifs.

The method according to the present invention can be used to purify any type of double-stranded DNA. An example of the latter is circular DNA, such as a plasmid, generally carrying one or more genes of therapeutic importance. This plasmid may also carry an origin of replication, a marker gene, and the like. The method of the invention may be applied directly to a cell lysate. In this embodiment, the plasmid, amplified by transformation followed by cell culture, is purified directly after lysis of the cells. The method of the invention may also be applied to a clear lysate, that is to say to the supernatant obtained after neutralization and centrifugation of the cell lysate. It may quite obviously be applied also to a solution prepurified by known methods. This method also enables linear or circular DNA carrying a sequence of importance to be purified from a mixture comprising DNAs of different sequences. The method according to the invention can also be used for the purification of double-stranded DNA.

The cell lysate can be a lysate of prokaryotic or eukaryotic cells.

As regards prokaryotic cells, the bacteria *E. coli, B. subtilis, S. typhimurium* or *Strepomyces* may be mentioned as examples. As regards eukaryotic cells, animal cells, yeasts, fungi, and the like, may be mentioned, and more especially *Kluyveromyces* or *Saccharomyces* yeasts or COS, CHO, C127, NIH3T3, and the like, cells.

The method of the invention is especially advantageous, since it enables plasmid DNA of very high purity to be obtained rapidly and simply. In particular, as illustrated in the examples, this method enables the plasmid DNA in question to be separated effectively from contaminating components such as fragmented chromosomal DNA, endotoxins, proteins, nucleases, and the like. More especially, the method of the invention enables preparation of double-stranded DNA, in particular that of plasmid origin, having a chromosomal DNA content of less than or equal to 0.5% to be obtained. Still more preferably, the DNA preparations obtained have a chromosomal DNA content of less than or equal to 0.2%. The present invention hence describes compositions comprising plasmid DNA which can be used pharmaceutically, in particular in gene or cell therapy. In this connection, the subject of the invention is also a pharmaceutical composition comprising double-stranded DNA, linear or of plasmid origin, prepared according to the method described above.

The invention also relates to plasmid DNA preparations having a chromosomal DNA content of less than or equal to 0.5%, preferably less than or equal to 0.2% and still more preferably less than or equal to 0.1%, and still more preferably less than or equal to 0.01%. As exemplified below, a triplex affinity interaction step has been incorporated in a purification process downstream of classical chromatographic steps. This affinity step significantly improves the purity of the plasmid preparation, whatever its initial purity. The formation of a triplex structure between an oligonucleotide (covalently bound to a chromatography support) and the plasmid of interest relies upon the presence on the plasmid of a sequence that can form a triplex structure with the oligonucleotide. This triplex structure is stable at acidic pH only, where the cytosines of the oligonucleotide are protonated. Then, plasmid DNA is eluted of the column simply by raising the pH to neutral.

The compositions can contain plasmid DNA which is "naked" or combined with transport carriers such as liposomes, nanoparticles, cationic lipids, polymers, recombinant viruses or proteins, and the like.

In one embodiment, the method according to the present invention can be used to purify one type of double-stranded DNA from a mixture comprising two or more double-stranded DNAs of different types and sequences. This method may be applied directly to a cell lysate, in which the double-stranded DNAs, amplified through cell culture, are purified after lysing the cultured cells. This method may also be applied to a clear lysate, i.e., to the supernatant obtained after neutralization and centrifugation of the cell lysate. The method may further be applied to a prepurified solution.

More precisely, the method for purifying a first double-stranded DNA from a solution containing first and second double-stranded DNAs, comprises (i) passing the solution through a first support comprising a covalently coupled oligonucleotide capable of forming a triple helix with the second double-stranded DNA by hybridization with a specific sequence therein, (ii) recovering the solution that passes through the first support, which will be enriched with unbound, first double-stranded DNA, and (iii) passing the recovered solution through a second support comprising a covalently coupled oligonucleotide capable of forming a triple helix by hybridization with a specific sequence of said first double-stranded DNA. Following an optional washing step, the first double-stranded DNA can be eluted from the second support. Using this double purification method, the first double-stranded DNA can be recovered from the second support without any detectable levels of the second double-stranded DNA.

In a specific embodiment of the present invention, the first double-stranded DNA molecule is a pCOR plasmid having a specific sequence 5'-AAGAAAAAAAAGAA-3' (SEQ ID NO: 29), which forms a stable triplex structure with an oligonucleotide having a sequence 5'-TTCTTTTTTTCTT-3' (SEQ ID NO: 30). The second double-stranded DNA molecule is a ColE1-derived plasmid having a specific sequence 5'-AGAAAAGGA-3' (SEQ ID NO: 27), which forms a triplex with an oligonucleotide having a sequence 5'-TCTTTTTTCCT-3' (SEQ ID NO: 28). Accordingly, the pCOR plasmid is advantageously purified from a solution containing other plasmids such as ColE1-derived plasmids by using the double purification method according to the present invention.

The present application will be described in greater detail by means of the examples which follow, which are to be regarded as illustrative and non-limiting.

DETAILED DESCRIPTION

General Techniques of Cloning and Molecular Biology

The traditional methods of molecular biology, such as digestion with restriction enzymes, gel electrophoresis, transformation in *E. coli*, precipitation of nucleic acids and the like, are described in the literature (Maniatis et al., T., E. F. Fritsch, and J. Sambrook, 1989. Molecular cloning: a laboratory manual, second edition. Cold Spring Harbor Laboratory, Cold Spring Harbor Laboratory Press, New York; Ausubel F. M., R Brent, R. E. Kinston, D. D. Moore, J. A. Smith, J. G. Seidman and K. Struhl. 1987. Current protocols in molecular biology 1987-1988. John Willey and Sons, New York.). Nucleotide sequences were determined by the chain termination method according to the protocol already published (Ausubel et al., 1987).

Restriction enzymes were supplied by New England Biolabs, Beverly, Mass. (Biolabs).

To carry out ligations, DNA fragments are incubated in a buffer comprising 50 mM Tris-HCl pH 7.4, 10 mM $MgCl_2$, 10 mM DTT, 2 mM ATP in the presence of phage T4 DNA ligase (Biolabs).

Oligonucleotides are synthesized using phosphoramidite chemistry with the phosphoramidites protected at the β position by a cyanoethyl group (Sinha, N. D., J. Biernat, J.

McManus and H. Köster, 1984. Polymer support oligonucleotide synthesis, XVIII: Use of β-cyanoethyl-N,N-dialkylamino-/N-morphohno phosphoramidite of deoxynucleosides for the synthesis of DNA fragments simplifying deprotection and isolation of the final product. Nucl. Acids Res., 12, 4539-4557: Giles, J. W. 1985. Advances in automated DNA synthesis. Am. Biotechnol., November/December) with a Biosearch 8600 automatic DNA synthesizer, using the manufacturer's recommendations.

Ligated DNAs or DNAs to be tested for their efficacy of transformation are used to transform the following strain rendered competent: E. coli DH5α[F/endA1, hsdR17, supE44, thi-1, recA1, gyrA96, relA1, Δ(lacZYA-arqF)U169, deoR, Φ80dlac, (lacZΔM15)] (for any Col E1 plasmid); or E. coli XAC-pir (for any pCor-derived plasmid).

Minipreparations of plasmid DNA are made according to the protocol of Klein et al., 1980.

LB culture medium is used for the growth of E. coli strains (Maniatis et al., 1982). Strains are incubated at 37° C. Bacteria are plated out on dishes of LB medium supplemented with suitable antibiotics.

Example 1

1.1. Preparation of the Column

Equipment

The column used is a 1 ml HiTrap column activated with NHS (N-hydroxysuccinimide, Pharmacia) connected to a peristaltic pump (output <1 ml/min. The specific oligonucleotide used possesses an $NH_2$ group at the 5' end, its sequence is as follows:

```
                                        (SEQ ID NO: 1)
5'-GAGGCTTCTTCTTCTTCTTCTTCTT-3'
```

The buffers used in this example are the following:
Coupling buffer: 0.2 M $NaHCO_3$, 0.5 M NaCl, pH 8.3.
Buffer A: 0.5 M ethanolamine, 0.5 M NaCl, pH 8.3.
Buffer B: 0.1 M acetate, 0.5 M NaCl, pH 4.
Method:
The column is washed with 6 ml of 1 mM HCl, and the oligonucleotide diluted in the coupling buffer (50 nmol in 1 ml) is then applied to the column and left for 30 minutes at room temperature. The column is washed three times in succession with 6 ml of buffer A and then 6 ml of buffer B. The oligonucleotide is thus bound covalently to the column through a CONH link. The column is stored at 4° C. in PBS, 0.1% $NaN_3$, and may be used at least four times.

1.2. Construction of Plasmids

The following two oligonucleotides were synthesized.
oligonucleotide 4817:

```
                                        (SEQ ID NO: 9)
5'-GATCCGAAGAAGAAGAAGAAGAAGAAGAAGAAGAAGAAGAAGA
AGAA GAAGAAGG-3'
``` oligonucleotide 4818:

```
                                       (SEQ ID NO: 10)
5'-AATTCCTTCTTCTTCTTCTTCTTCTTCTTCTTCTTCTTCTTCT
TCTTCTTCTTCG-3'
```

These oligonucleotides, when hybridized and cloned into a plasmid, introduce a homopurine-homopyrimidine sequence $(GAA)_{17}$ (SEQ ID NO: 33) into the corresponding plasmid, as described above.

The sequence corresponding to these two hybridized oligonucleotides was cloned at the multiple cloning site of plasmid pBKS+ (Stratagene Cloning System, La Jolla Calif.), which carries an ampicillin-resistance gene. To this end, the oligonucleotides were hybridized in the following manner: one µg of these two oligonucleotides were placed together in 40 ml of a final buffer comprising 50 mM Tris-HCl pH 7.4, 10 mM $MgCl_2$. This mixture was heated to 95° C. and was then placed at room temperature so that the temperature would fall slowly. Ten ng of the mixture of hybridized oligonucleotides were ligated with 200 ng of plasmid pBKS+ (Stratagene Cloning System, La Jolla Calif.) digested with BamHI and EcoRI in 30 µl final. After ligation, an aliquot was transformed into DH5a. The transformation mixtures were plated out on L medium supplemented with ampicillin (50 mg/l) and X-gal (20 mg/l). The recombinant clones should display an absence of blue coloration on this medium, contrary to the parent plasmid (pBKS+) which permits α-complementation of fragment ω of E. coli β-galactosidase. After minipreparation of plasmid DNA from 6 clones, they all displayed the disappearance of the PstI site located between the EcoRI and BamHI sites of pBKS+, and an increase in molecular weight of the 448-bp PvuII band containing the multiple cloning site. One clone was selected and the corresponding plasmid was designated pXL2563. The cloned sequence was verified by sequencing using primer −20 (5'-TGACCGGCAG-CAAAATG-3' (SEQ ID NO: 11)) (Viera J. and J. Messing. 1982. The pUC plasmids, an M13 mp 7-derived system for insertion mutagenesis and sequencing with synthetic universal primers. Gene, 19, 259-268) for plasmid pBKS+(Stratagene Cloning System, La Jolla Calif.). Plasmid pXL2563 was purified according to Wizard Megaprep kit (Promega Corp. Madison, Wis.) according to the supplier's recommendations. This plasmid DNA preparation was used thereafter in examples described below.

1.3. Plasmid Purification

Equipment:
Plasmid pXL2563 (described in 1.2) was purified on the HiTrap column coupled to the oligonucleotide, described in 1.1., from a solution also containing plasmid pBKS+. The buffers used in this purification are the following:
Buffer F: 2 M NaCl, 0.2 M acetate, pH 4.5 to 5.
Buffer E: 1 M Tris-HCl, pH 9, 0.5 mM EDTA.
Method:
The column is washed with 6 ml of buffer F, and the plasmids (20 µg of pXL2563 and 20 µg of pBKS+ in 400 µl of buffer F) are applied to the column and incubated for 2 hours at room temperature. The column is washed with 10 ml of buffer F and elution is then carried out with buffer E. The plasmids are detected after electrophoresis on 1% agarose gel and ethidium bromide staining. The proportion of the plasmids in the solution is estimated by measuring their transforming activity on E. coli.
Result:
Starting from a mixture containing 30% of pXL2563 and 70% of pBKS+, a solution containing 100% of pXL2563 is recovered at the column outlet. The purity, estimated by the OD ratio at 260 and 280 nm, rises from 1.9 to 2.5, which indicates that contaminating proteins are removed by this method.

Example 2

2.1.—This example describes a plasmid DNA purification experiment. Coupling of the oligonucleotide (5'-GAGGCT-TCTTCTTCTTCTTCTTCTT-3' (SEQ ID NO: 1)) to the column is performed as described in Example 1. For the coupling, the oligonucleotide is modified at the 5' end with an amine group linked to the phosphate of the spacer by an arm containing 6 carbon atoms (Modified oligonucleotide Eurogentec SA, Belgium). Plasmid pXL2563 was purified using the Wizard Megaprep kit (Promega Corp., Madison, Wis.) according to the supplier's recommendations. The buffers used in this example are the following:

Buffer F: 0-2 M NaCl, 0.2 M acetate, pH 4.5 to 5.
Buffer E: 1 M Tris-HCl pH 9, 0.5 mM EDTA.

The column is washed with 6 ml of buffer F, and 100 µg of plasmid pXL2563 diluted in 400 µl of buffer F are then applied to the column and incubated for 2 hours at room temperature. The column is washed with 10 ml of buffer F and elution is then carried out with buffer E. The plasmid is quantified by measuring optical density at 260 nm.

In this example, binding is carried out in a buffer whose molarity with respect to NaCl varies from 0 to 2 M (buffer F). The purification yield decreases when the molarity of NaCl falls. The pH of the binding buffer can vary from 4.5 to 5, the purification yield being better at 4.5. It is also possible to use another elution buffer of basic pH: elution was thus carried out with a buffer comprising 50 mM borate, pH 9, 0.5 mM EDTA.

2.2.—Coupling of the oligonucleotide (5'-GAGGCTTCT-TCTTCTTCTTCTTCTT-3' (SEQ ID NO: 1)) to the column is carried out as described in Example 1. Plasmid pXL2563 was purified using the Wizard Megaprep kit (Promega Corp., Madison, Wis.) according to the supplier's recommendations. The buffers used in this example are the following:

Buffer F: 0.1 M NaCl, 0.2 M acetate, pH 5.
Buffer E: 1 M Tris-HCl pH 9, 0.5 mM EDTA.

The column is washed with 6 ml of buffer F, and 100 µg of plasmid pXL2563 diluted in 400 µl of buffer F are then applied to the column and incubated for one hour at room temperature. The column is washed with 10 ml of buffer F and elution is then carried out with buffer E. The content of genomic or chromosomal *E. coli* DNA present in the plasmid samples before and after passage through the oligonucleotide column is measured. This genomic DNA is quantified by PCR using primers in the *E. coli* galK gene. According to the following protocol: The sequence of these primers is described by Debouck et al. (Nucleic Acids Res. 1985, 13, 1841-1853):

```
                                        (SEQ ID NO: 24)
5'-CCG AAT TCT GGG GAC CAA AGC AGT TTC-3'
and (SEQ ID NO: 25)
5'-CCA AGC TTC ACT GTT CAC GAC GGG TGT-3'.
```

The reaction medium comprises, in 25 µl of PCR buffer (Promega France, Charbonnières): 1.5 mM $MgCl_2$; 0.2 mM dXTP (Pharmacia, Orsay); 0.5 µM primer; 20 U/ml Taq polymerase (Promega). The reaction is performed according to the sequence:

5 min at 95° C.
30 cycles of 10 sec at 95° C.
30 sec at 60° C.
1 min at 78° C.
10 min at 78° C.

The amplified DNA fragment 124 base pairs in length is separated by electrophoresis on 3% agarose gel in the presence of SybrGreen I (Molecular Probes, Eugene, USA), and then quantified by reference to an Ultrapur genomic DNA series from *E. coli* strain B (Sigma, ref D4889).

There is 1% of chromosomal DNA in the sample applied to the column, and 0.2% in the sample purified on the oligonucleotide column.

Example 3

Experiment on Clear Lysate

This example describes plasmid DNA purification from a clear lysate of bacterial culture, on the so-called "miniprep" scale: 1.5 ml of an overnight culture of DH5a strains containing plasmid pXL2563 are centrifuged, and the pellet is resuspended in 100 µl of 50 mM glucose, 25 mM Tris-HCl, pH 8, 10 mM EDTA. 200 µl of 0.2 M NaOH, 1% SDS are added, the tubes are inverted to mix, 150 µl of 3 M potassium acetate, pH 5 are then added and the tubes are inverted to mix. After centrifugation, the supernatant is recovered and loaded onto the oligonucleotide column obtained as described in Example 1. Binding, washes and elution are identical to those described in Example 1. Approximately 1 µg of plasmid is recovered from 1.5 ml of culture. The plasmid obtained, analysed by agarose gel electrophoresis and ethidium bromide staining, takes the form of a single band of "supercoiled" circular DNA. No trace of high molecular weight (chromosomal) DNA or of RNA is detectable in the plasmid purified by this method. The ratio of the optical densities at 260 and 280 µm is greater than 2.

Example 4

4.1: This example describes a plasmid DNA purification experiment carried out under the same conditions as Example 3, starting from 20 ml of bacterial culture of DH5a strains containing plasmid pXL2563. The cell pellet is taken up in 1.5 ml of 50 mM glucose, 25 mM Tris-HCl, pH 8, 10 mM EDTA. Lysis is carried out with 2 ml of 0.2 M NaOH, 1% SDS, and neutralization with 1.5 ml of 3 M potassium acetate, pH 5. The DNA is then precipitated with 3 ml of 2-propanol, and the pellet is taken up in 0.5 ml of 0.2 M sodium acetate, pH 5, 0.1 M NaCl and loaded onto the oligonucleotide column obtained as described in Example 1. Binding, washing of the column and elution are carried out as described in Example 1, except for the washing buffer, the molarity of which with respect to NaCl is 0.1M. Approximately 16 µg of plasmid DNA are obtained. The plasmid obtained, analysed by agarose gel electrophoresis and ethidium bromide staining, takes the form of a single band of "supercoiled" circular DNA. No trace of high molecular weight (chromosomal) DNA or of RNA is detectable in the purified plasmid. Digestion of the plasmid with a restriction enzyme gives a single band at the expected molecular weight of 3 kilobases. The protein concentration in the samples falls from 125 µg/ml in the clear lysate to less than 1 µg/ml in the purified plasmid (Micro-BCA assay, Pierce). The endotoxin concentration, estimated by LAL assay (Biosepra) is divided by a factor of greater than 10 in the purified plasmid, relative to the starting clear lysate.

4.2: The plasmid used contains a cassette containing the cytomegalovirus promoter, the gene coding for luciferase and the homopurine-homopyrimidine sequence $(GAA)_{17}$ (SEQ ID NO: 33) originating from plasmid pXL2563. The strain DH1 (Maniatis et al., 1989) containing this plasmid is cultured in a 7-litre fermenter. A clear lysate is prepared from 200 grams of cells: the cell pellet is taken up in 2 litres of 25 mM Tris, pH 6.8, 50 mM glucose, 10 mM EDTA, to which 2 litres of 0.2 M NaOH, 1% SDS, are added. The lysate is neutralized by adding one litre of 3M potassium acetate. After diafiltration, 4 ml of this lysate are applied to a 5 ml HiTrap-NHS column coupled to the oligonucleotide of sequence 5'-GAG-GCTTCTTCTTCTTCTTCTTCTT-3' (SEQ ID NO: 1), according to the method described in Example 1.1. Washing and elution are carried out as described in Example 1. Approximately 400 micrograms of plasmid are recovered. The level of genomic DNA in this sample, measured by the technique described in Example 2.2, is 0.1%.

Example 5

Use of a Modified Oligonucleotide

This example describes the use of an oligonucleotide bearing methylated cytosines. The sequence of the oligonucleotide used is as follows:

```
                                              (SEQ ID NO: 12)
5'-GAGG^MeCTT^MeCTT^MeCTT^MeCTT^MeCCT^MeCTT^MeCTT-3'
```

This oligonucleotide possesses an $NH_2$ group at the 5' end. $^{Me}C$=5-methylcytosine. This oligonucleotide enables plasmid pXL2563 to be purified under the conditions of Example 1 with a binding buffer of pH 5 (the risk of degradation of the plasmid is thereby decreased).

Example 6

In the above examples, the oligonucleotide used is modified at the 5'-terminal end with an amine group linked to the phosphate through an arm containing 6 carbon atoms: $NH_2$—$(CH_2)_6$. In this example, the amine group is linked to the phosphate of the 5'-terminal end through an arm containing 12 carbon atoms: $NH_2$—$(CH_2)_{12}$. Coupling of the oligonucleotide and passage through the column are carried out as described in Example 2 with a buffer F: 2 M NaCl, 0.2 M acetate, pH 4.5. This oligonucleotide makes it possible to have better purification yields: a 53% yield is obtained, whereas, with the oligonucleotide containing 6 carbon atoms, this yield is of the order of 45% under the same conditions.

Example 7

Following the cloning strategy described in Example 1.2, another two plasmids carrying homopurine-homopyrimidine sequences were constructed: the plasmid pXL2725 which contains the sequence $(GGA)_{16}$, (SEQ ID NO: 34) and the plasmid pXL2726 which contains the sequence $(GA)_{25}$ (SEQ ID NO: 35).

Example 7.1

Construction of the Plasmids

Plasmids pXL2725 and pXL2726, analogous to plasmid pXL2563, were constructed according to the cloning strategy described in Example 1.2, using the following oligonucleotide pairs:

```
5986: 5'-GATCC(GA)25GGG-3'  (SEQ ID NO: 13)

5987: 5'-AATTCCC(TC)25G-3'  (SEQ ID NO: 14)
```

```
5981: 5'-GATCC(GGA)17GG-3'  (SEQ ID NO: 15)

5982: 5'-AATT(CCT)17CCG-3'  (SEQ ID NO: 16)
```

The oligonucleotide pair 5986 and 5987 was used to construct plasmid pXL2726 by cloning the oligonucleotides at the BamHI and EcoRI sites of pBKS+(Stratagene Cloning System, La Jolla Calif.), while the oligonucleotides 5981 and 5982 were used for the construction of plasmid pXL2725. The same experimental conditions as for the construction of plasmid pXL2563 were used, and only the oligonucleotide pairs were changed. Similarly, the cloned sequences were verified by sequencing on the plasmids. This enabled it to be seen that plasmid pXL2725 possesses a modification relative to the expected sequence: instead of the sequence GGA repeated 17 times, there is $GGAGA(GGA)_{15}$ (SEQ ID NO: 17).

Example 7.2

Preparation of the Columns and Purification

The oligonucleotides forming triple helices with these homopurine sequences were coupled to HiTrap columns according to the technique described in Example 1.1. The oligonucleotide of sequence 5'-AATGCCTCCTCCTCCTC-CTCCTCCT-3' (SEQ ID NO: 18) was used for the purification of plasmid pXL2725, and the oligonucleotide of sequence. 5'-AGTGCTCTCTCTCTCTCTCTCTCT-3' (SEQ ID NO: 19) was used for the purification of plasmid pXL2726.

The two columns thereby obtained enabled the corresponding plasmids to be purified according to the technique described in Example 2, with the following buffers:
Buffer P: 2 M NaCl, 0.2 M acetate, pH 4.5.
Buffer E: 1 M Tris-HCl, pH 9, 0.5 mM EDTA.
The yields obtained are 23% and 31% for pXL2725 and pXL2726, respectively.

Example 8

This example illustrates the influence of the length of the specific sequence present in the plasmid on the purification yields.

Example 8.1

Construction of the Plasmids

The reporter gene used in these experiments to demonstrate the activity of the compositions of the invention is the gene coding for luciferase (Luc).

The plasmid pXL2621 contains a cassette containing the 661-bp cytomegalovirus (CMV) promoter, extracted from pcDNA3 (Invitrogen Corp., San Diego, Calif.) by cleavage with the restriction enzymes MluI and HindIII, cloned upstream of the gene coding for luciferase, at the MluI and HindIII sites, into the vector pGL basic Vector (Promega Corp., Madison, Wis.). This plasmid was constructed using standard techniques of molecular biology.

The plasmids pXL2727-1 and pXL2727-2 were constructed in the following manner:

Two micrograms of plasmid pXL2621 were linearized with BamHI; the enzyme was inactivated by treatment for 10 min at 65° C.; at the same time, the oligonucleotides 6006 and 6008 were hybridized as described for the construction of plasmid pXL2563.

6006: 5'-GATCT(GAA)$_{17}$CTGCAGATCT-3' (SEQ ID NO: 20)

6008: 5'-GATCAGATCTGCAG(TTC)$_{17}$A-3'. (SEQ ID NO: 21)

This hybridization mixture was cloned at the BamHI ends of plasmid pXL2621 and, after transformation into DH5a, recombinant clones were identified by PstI enzymatic restriction analysis, since the oligonucleotides introduce a PstI site. Two clones were selected, and the nucleotide sequence of the cloned fragment was verified using the primer (6282, 5'-ACAGTCATAAGTGCGGCGACG-3' (SEQ ID NO: 22)) as a sequencing reaction primer (Viera J. and J. Messing, 1982. The pUC plasmids an M13 mp 7-derived system for insertion mutagenesis and sequencing with synthetic universal primers. Gene 19:259-268).

The first clone (pXL2727-1) contains the sequence GAA repeated 10 times. The second (pXL2727-2) contains the sequence

5'-GAAGAAGAG(GAA)$_7$GGAAGAGAA-3'. (SEQ ID NO: 23)

Example 8.2

Preparation of the Columns and Purification

A column such as the one described in Example 1, and which is coupled to the oligonucleotide 5'-GAGGCTTCT-TCTTCTTCTTCTT-3' (SEQ ID NO: 1), is used.

The plasmid pXL2727-1 carries 14 repeats of the sequence GAA. The oligonucleotide described above, which contains only 7 repeats of the corresponding hybridization sequence CTT, can hence hybridize with the plasmid at 8 different positions. Plasmid pXL2727-2, in contrast, possesses a hybridizing sequence (GAA)$_7$ (SEQ ID NO: 36) of the same length as that of the oligonucleotide bound to the column. This oligonucleotide can hence hybridize at only one position on pXL2727-2.

The experiment is identical to the one described in Example 2, with the following buffers:
Buffer F: 2 M NaCl, 0.2 M acetate, pH 4.5.
Buffer E: I M Tris-HCl, pH 9, 0.5 mM EDTA.

The purification yield is 29% with plasmid pXL2727-1 and 19% with pXL2727-2.

Example 8.3

In Vitro Transfection of Mammalian Cells

The cells used are NIH 3T3 cells, inoculated on the day before the experiment into 24-well culture plates on the basis of 50,000 cells/well. The plasmid is diluted in 150 M NaCl and mixed with the lipofectant RPR115335. A lipofectant positive charges/DNA negative charges ratio equal to 6 is used. The mixture is vortexed, left for ten minutes at room temperature, diluted in medium without foetal calf serum and then added to the cells in the proportion of 1 µg of DNA per culture well. After two hours at 37° C., 10% volume/volume of foetal calf serum is added and the cells are incubated for 48 hours at 37° C. in the presence of 5% of $CO_2$. The cells are washed twice with PBS and the luciferase activity is measured according to the protocol described (Promega kit, Promega Corp. Madison, Wis.) on a Lumat LB9501 luminometer (EG and G Berthold, Evry). Plasmid pXL2727-1, purified as described in Example 8.2, gives transfection yields twice as large as those obtained with the same plasmid purified using the Wizard Megaprep kit (Promega Corp. Madison, Wis.).

Example 9

Purification of pCOR-Derived Plasmids

The following example demonstrates the purification of pCOR-derived plasmids using triple-helix affinity chromatography. This technology has been shown to remove nucleic acid contaminants particularly host genomic DNA and RNA) down to levels that have not been achieved with conventional chromatography methods.

A triplex affinity gel was synthesized with Sephacryl S-1000 SF (Amersham-Pharmacia Biotech) as the chromatography matrix. Sephacryl S-1000 was first activated with sodium m-periodate (3 mM, room temperature, 1 h) in 0.2 M sodium acetate (pH 4.7). Then the oligonucleotide was coupled through its 5'—$NH_2$ terminal moiety to aldehyde groups of the activated matrix by reductive amination in the presence of ascorbic acid (5 mM) as described previously for the coupling of proteins (Hornsey et al., J. Immunol. Methods, 1986, 93, 83-88). The homopyrimidine oligonucleotide used for these experiments (from Eurogentec, HPLC-purified) had a sequence which was complementary to a short 14-mer homopurine sequence (5'-AAGAAAAAAAAGAA-3') (SEQ ID NO: 29) present in the origin of replication (ori) of the pCOR plasmid (Soubrier et al., Gene Therapy, 1999, 6, 1482-1488). As discussed above, the sequence of the homopyrimidine oligonucleotide is 5'-TTCTTTTTTTTCTT-3' (SEQ ID NO: 30).

The following plasmids were chromatographed: pXL3296 (pCOR with no transgene, 2.0 kpb), pXL3179 (pCOR-FGF, 2.4 kpb), pXL3579 (pCOR-VEGFB, 2.5 kbp), pXL3678 (pCOR-AFP, 3.7 kbp), pXL3227 pCOR-lacZ 5.4 kbp) and pXL3397 (pCOR-Bdeleted FVIII, 6.6 kbp). All these plasmids were purified by two anion-exchange chromatography steps from clear lysates obtained as described in example 4. Plasmid pBKS+ (pBluescript II KS+from Stratagene), a ColE1-derived plasmid, purified by ultracentrifugation in CsCl was also studied. All plasmids used were in their supercoiled (>95%) topological state.

In each plasmid DNA purification experiment, 300 µg of plasmid DNA in 6 ml of 2 M NaCl, 0.2 M potassium acetate (pH 5.0) was loaded at a flow rate of 30 cm/h on an affinity column containing the above-mentioned oligonucleotide 5'-TTCTTTTTTTTCTT-3' (SEQ ID NO: 30). After washing the column with 5 volumes of the same buffer, bound plasmid was eluted with 1 M Tris/HCl, 0.5 mM EDTA (pH 9.0) and quantitated by UV (260 µm) and ion-exchange chromatography with a Millipore Gen-Pak column (Marquet et al., BioPharm, 1995, 8, 26-37). Plasmid recoveries in the fraction collected were 207 µg for pXL3296, 196 µg for pXL3179, 192 µg for pXL3579, 139 µg for pXL3678, 97 µg for pXL 3227, and 79 µg for pXL 3397.

No plasmid binding could be detected (<3 µg) when pBKS was chromatographed onto this column. This indicates that oligonucleotide 5'-TTCTTTTTTTTCTT-3' (SEQ ID NO: 30) makes stable triplex structures with the complementary 14-mer sequence 5'-AAGAAAAAAAAGAA-3' (SEQ ID NO: 29) present in pCOR (oriγ), but not with the closely related sequence 5'-AGAAAAAAGGA-3' (SEQ ID NO: 27) present in pBKS. This indicates that the introduction of a single non-canonical triad (T*GC in this case) results in a complete destabilization of the triplex structure.

As a control, no plasmid binding (<1 μg) was observed when pXL3179 was chromatographed on a blank column synthesized under strictly similar conditions but without oligonucleotide.

By operating this affinity purification column in the conditions reported here, the level of contamination by host genomic DNA was reduced from 2.6% down to 0.07% for a preparation of pXL3296. Similarly the level of contamination by host DNA was reduced from 0.5% down to 0.008% for a preparation of pXL3179 when the sample was chromatographed through the same affinity column. In addition, the level of contamination by RNA was largely reduced from 43% RNA down to 0.2% RNA in a preparation of pXL3179 by using this affinity purification column.

In addition, plasmid PXL3579 recovery was less than 8% when oligonucleotide 5'-TTCTTTTTTTTCTT-3' (SEQ ID NO: 30) was replaced by oligonucleotide 5'-TTTTTTTTCTT-3' (SEQ ID NO: 31) on the affinity column. While the oligonucleotide as set forth in SEQ ID NO: 31 is complementary to a portion of the VEGFB sequence within pXL3579 (i.e., nucleotides 379 to 389 relative to ATG), no significant triplex affinity occurs. This indicates that this affinity purification requires a non-random homopurine-homopyrimidine DNA sequence.

Example 10

Purification of a ColE1-Derived Plasmid

The following example demonstrates the purification of ColE1-derived plasmids using triple-helix affinity chromatography. This technology has been shown to remove nucleic acid contaminants (particularly host genomic DNA and RNA) down to levels that have not been achieved with conventional chromatography methods.

A triplex affinity gel was synthesized by coupling of an oligonucleotide having the sequence 5'-TCTTTTTTCCT-3' (SEQ ID NO: 28) onto periodate-oxidized Sephacryl S-1000 SF as described in Example 9.

Plasmids pXL3296 (pCOR with no transgene) and pBKS, a ColE1-derived plasmid, were chromatographed on a 11-ml column containing oligonucleotide 5'-TCTTTTTTTCCT-3' (SEQ ID NO: 28) in conditions described in Example 9. Plasmid recoveries in the fraction collected were 175 μg for pBKS and <1 μg for pXL3296. This indicates that oligonucleotide 5'-TCTTTTTTTCCT-3' (SEQ ID NO: 28) makes stable triplex structures with the complementary 12-mer sequence (5'-AGAAAAAAAGGA-3') (SEQ ID NO: 27) present in pBKS, but not with the very closely related 12-mer sequence (5'-AGAAAAAAAGA-3') (SEQ ID NO: 32) present in pCOR. This indicates that the introduction of a single non-canonical triad (C*AT in this case) may result in complete destabilization of the triplex structure.

Example 11

Double Purification Method

The following example demonstrates the purification of a supercoiled double-stranded DNA molecule, such as pXL3296, in a mixture containing another supercoiled double-stranded molecule, such as pBSK, using triple helix affinity chromatography. Both double-stranded DNA molecules may have a similar size, but each DNA molecule contains a unique sequence that is capable of forming a triple helix with a different target sequence. As previously discussed, molecules such as pXL3296 contain a sequence 5'-AAGAAAAAAAAGAA-3' (SEQ ID NO: 29), but do not contain the sequence 5'-AGAAAAAAAGGA-3' (SEQ ID NO: 27). In contrast, molecules such as pBSK contain SEQ ID NO: 27, but do not contain SEQ ID NO: 29.

In a first step, the mixture containing pXL3296 and pBSK was loaded on a first affinity column containing the oligonucleotide 5'-TCTTTTTTTCCTT-3' (SEQ ID NO: 28), such as the column described in Example 10. The solution was passed through the first column which contained unbound DNA molecules. In the second step, the unbound DNA molecules from the first step were loaded on a second affinity column containing the oligonucleotide 5'-TTCTTTTTTTTCTT-3' (SEQ ID NO: 30), such as the column described in Example 9. The second column was then washed and the bound molecules were eluted, as described in Example 9. Only pXL3296 molecules eluted from the second column. No pBSK molecules were detected in the eluate (i.e., the solution that elutes from the column) from the second column.

We claim:

1. A method of coupling an oligonucleotide to a purification support, wherein the support is a functionalized chromatographic support that comprises residues, comprising:
   a) activating the residues of the support, and
   b) contacting the activated residues of the support with the oligonucleotide to obtain covalent coupling directly between the oligonucleotide and the residues of the purification support;
wherein the oligonucleotide comprises a pyrimidine-rich sequence which forms a triple helix with a double-stranded DNA by hybridizing with a nucleotide sequence in the double-stranded DNA, wherein the support comprises a resin comprising hydroxyl residues activated by esterification with N-hydroxylsuccinimide, and wherein contacting the activated residues with the oligonucleotide creates a covalent amide coupling between the oligonucleotide and the residues of the support.

2. The method according to claim 1, wherein the resin is agarose, dextran, sephadex, or grafted or ungrafted silica.

3. A method of coupling an oligonucleotide to a purification support, wherein the support is a functionalized chromatographic support that comprises residues, comprising:
   a) activating the residues of the support, and
   b) contacting the activated residues of the support with the oligonucleotide to obtain covalent coupling directly between the oligonucleotide and the residues of the purification support;
wherein the oligonucleotide comprises a pyrimidine-rich sequence which forms a triple helix with a double-stranded DNA by hybridizing with a nucleotide sequence in the double-stranded DNA, wherein the support comprises a resin comprising diol residues activated by oxidation with sodium m-periodate, and wherein the oligonucleotide is coupled to the residues of the support by reductive amination in the presence of ascorbic acid.

4. The method according to claim 3, wherein the resin is agarose, dextran, sephadex, or grafted or ungrafted silica.

5. A support comprising a covalently coupled oligonucleotide, wherein the oligonucleotide comprises a pyrimidine-rich sequence which forms a triple helix with a double-stranded DNA by hybridizing with a nucleotide sequence in the double-stranded DNA, wherein the oligonucleotide is covalently coupled directly to the purification support through a disulphide, thioether, ester, amide or amine link, and wherein the support is a functionalized chromatographic support comprising agarose, dextran, or sephadex.

6. A method of coupling an oligonucleotide to a purification support, wherein the support comprises (1) residues and (2) agarose, dextran, or sephadex, comprising:

a) activating the residues of the support, and
b) contacting the activated residues of the support with the oligonucleotide to obtain covalent coupling directly between the oligonucleotide and the residues of the purification support;

wherein the oligonucleotide comprises a pyrimidine-rich sequence which forms a triple helix with a double-stranded DNA by hybridizing with a nucleotide sequence in the double-stranded DNA.

* * * * *